United States Patent [19]

Benson et al.

[11] Patent Number: 5,006,343
[45] Date of Patent: Apr. 9, 1991

[54] PULMONARY ADMINISTRATION OF PHARMACEUTICALLY ACTIVE SUBSTANCES

[76] Inventors: Bradley J. Benson; JoRae Wright, both of 170 Cresta Vista Dr., San Francisco, Calif. 94127

[21] Appl. No.: 295,926

[22] Filed: Dec. 29, 1988

[51] Int. Cl.$^5$ .............................................. A61K 37/22
[52] U.S. Cl. ................................... 424/450; 252/181; 264/4.6
[58] Field of Search ........................ 424/450; 252/181; 264/4.6

[56] References Cited

U.S. PATENT DOCUMENTS

| | | |
|---|---|---|
| 3,594,476 | 7/1971 | Merrill ................................ 252/181 |
| 4,571,334 | 2/1986 | Yoshida et al. . |
| 4,659,805 | 3/1987 | Schilling et al. . |
| 4,746,508 | 5/1988 | Carey et al. . |
| 4,765,987 | 8/1988 | Bonte et al. ......................... 424/450 |
| 4,828,844 | 5/1989 | Ronteen-Odenthal et al. .... 514/148 |

FOREIGN PATENT DOCUMENTS

| | | |
|---|---|---|
| 8701586 | 3/1987 | PCT Int'l Appl. . |
| 8804938 | 7/1988 | PCT Int'l Appl. . |

*Primary Examiner*—Merrell C. Cashion, Jr.
*Assistant Examiner*—P. L. Prater
*Attorney, Agent, or Firm*—Irell & Manella

[57] ABSTRACT

Pulmonary administration of a pharmaceutically active substance useful for local or systemic action which comprises, liposomes containing an effective amount of a pharmaceutically active substance, and an amount of alveolar surfactant protein effective to enhance transport of the liposomes across a pulmonary surface.

9 Claims, 7 Drawing Sheets

FIG. 1-1

```
MET Trp Leu Cys Pro Leu Ala Leu Asn Leu Ile Leu MET Ala Ala Ser Gly Ala Val Cys  -1
-20                                                                          Ala

Glu Val Lys Asp Val Cys Val Gly Ser Pro Gly Ile Pro Gly Thr Pro Gly Ser His Gly
+1

Leu Pro Gly Arg Asp Gly Arg Asp Gly Val Lys Gly Asp Pro Gly Pro Pro Gly Pro MET

Gly Pro Pro Gly Glu MET Pro Cys Pro Pro Gly Asn Asp Gly Leu Pro Gly Ala Pro Gly
                    Thr                         Asn

Ile Pro Gly Glu Cys Gly Lys Gly Glu Pro Gly Glu Arg Gly Pro Pro Gly Leu Pro Gly
Val             Arg                     Ala

Ala His Leu Asp Glu Leu Gln Ala Thr Leu His Asp Phe Arg His Gln Ile Leu Gln

Thr Arg Gly Ala Leu Ser Leu Gln Gly Ser Ile MET Thr Val Gly Glu Lys Val Phe Ser
```

FIG.1-2

Ser Asn Gly Gln Ser Ile Thr Phe Asp Ala Ile Gln Glu Ala Cys Ala Arg Ala Gly Gly

Arg Ile Ala Val Pro Arg Asn Pro Glu Glu Asn Glu Ala Ile Ala Ser Phe Val Lys Lys

Tyr Asn Thr Tyr Ala Tyr Val Gly Leu Thr Glu Gly Pro Ser Pro Gly Asp Phe Arg Tyr

Ser Asp Gly Thr Pro Val Asn Tyr Thr Asn Trp Tyr Arg Gly Glu Pro Ala Gly Arg Gly

Lys Glu Gln Cys Val Glu MET Tyr Thr Asp Gly Gln Trp Asn Asp Arg Asn Cys Leu Tyr

Ser Arg Leu Thr Ile Cys Glu Phe End
228

FIG.2-1

MET Ala Glu Ser His Leu Leu Leu Gln Trp Leu Leu Leu Leu Pro Thr Leu Cys Gly Pro
-200

Gly Thr Ala Ala Trp Thr Thr Ser Ser Leu Ala Cys Ala Gln Gly Pro Glu Phe Trp Cys

Gln Ser Leu Glu Gln Ala Leu Gln Cys Arg Ala Leu Gly His Cys Leu Gln Glu Val Trp

Gly His Val Gly Ala Asp Asp Leu Cys Gln Glu Cys Glu Asp Ile Val His Ile Leu Asn

Lys MET Ala Lys Glu Ala Ile Phe Gln Asp Thr MET Arg Lys Phe Leu Glu Gln Glu Cys

Asn Val Leu Pro Leu Lys Leu Leu MET Pro Gln Cys Asn Gln Val Leu Asp Asp Tyr Phe
                                                                          -1 +1

Pro Leu Val Ile Asp Tyr Phe Gln Asn Gln Ile Asp Ser Asn Gly Ile Cys MET His Leu

FIG.2-2

Gly Leu Cys Lys Ser Arg Gln Pro Glu Gln Glu Pro Gly MET Ser Asp Pro Leu

Pro Lys Pro Leu Arg Asp Pro Leu Pro Asp Lys Leu Val Leu Pro Val

Leu Pro Gly Ala Leu Gln Ala Arg Pro Gly His Thr Gln Asp Leu Ser Glu Gln Gln

Phe Pro Ile Pro Leu Pro Tyr Cys Trp Leu Cys Arg Ala Leu Ile Lys Arg Ile Gln Ala

MET Ile Pro Lys Gly Ala Leu Arg Val Ala Val Ala Gln Val Cys Arg Val Val Pro Leu

Val Ala Gly Gly Ile Cys Gln Cys Leu Ala Glu Arg Tyr Ser Val Ile Leu Leu Asp Thr

Leu Leu Gly Arg MET Leu Pro Gln Leu Val Cys Arg Leu Val Leu Arg Cys Ser MET Asp

FIG.2-3

Asp Ser Ala Gly Pro Arg Ser Pro Thr Gly Glu Trp Leu Pro Arg Asp Ser Glu Cys His

Leu Cys MET Ser Val Thr Thr Gln Ala Gly Asn Ser Ser Glu Gln Ala Ile Pro Gln Ala

MET Leu Gln Ala Cys Val Gly Ser Trp Leu Asp Arg Glu Lys Cys Lys Gln Phe Val Glu

Gln His Thr Pro Gln Leu Leu Thr Leu Val Pro Arg Gly Trp Asp Ala His Thr Thr Cys

Gln Ala Leu Gly Val Cys Gly Thr MET Ser Ser Pro Leu Gln Cys Ile His Ser Pro Asp

Leu End
181

FIG.3

```
MET Asp Val Gly Ser Lys Glu Val Leu MET Glu Ser Pro Asp Tyr Ser Ala Ala Pro
 1                                                                   19  20
              N Term
Arg Gly Arg Phe Gly Ile Pro Cys Cys Pro Val His Leu Lys Arg Leu Leu Ile Val Val
 21  22  23  24  25  26  27  28  29  30  31  32  33  34  35  36  37
                                                         C Term
Val Val Val Val Leu Ile Val Val Ile Val Gly Ala Leu Leu Leu MET Gly Leu His MET
                                                         55  56  57  58  59  60
Ser Gln Lys His Thr Glu MET Val Leu Glu Met Ser Ile Gly Ala Pro Glu Ala Gln
                                                             74
 65                      70
```

PULMONARY ADMINISTRATION OF PHARMACEUTICALLY ACTIVE SUBSTANCES

TECHNICAL FIELD

This invention relates to the field of pharmaceutical administration. More specifically it relates to pulmonary administration of pharmaceutically active substances.

BACKGROUND ART

The mode of administration of a drug can affect its bioavailability and pharmacokinetic profile, as well as patient compliance. Patient compliance is best when the mode of administration is convenient and does not involve patient discomfort. Oral administration is often the preferred mode.

Despite the advantages of oral administration, it is still unworkable for many drugs. One problem with oral administration arises because there can be extensive metabolism of a drug during transit from the gastrointestinal tract to the general circulation. For example, the intestinal mucosa, through which an orally administered drug passes before it enters the circulatory system, is enzymatica))y very active and can thus metabolize a drug in many ways. Therefore, bioavailability of orally administered drugs can be very low.

With the advent of recombinant DNA technology, many more peptides are available for pharmaceutical use than ever before. However, oral administration of peptides is particularly problematic because peptide bonds are cleaved by proteases secreted into the gut, as part of the digestive process. The only broadly applicable means of administration of peptides at this time is parenteral administration. This is not always a practical or desirable route, especially if the drug is required to be administered chronically, such as in the case of insulin treatment for diabetes. Many individuals are reluctant or unable to self-inject a parenterally-formulated drug on a routine basis.

Some of the shortcomings of oral and parenteral administration can be circumvented by administering the drug by a route which avoids digestive and gut-wall metabolism, and also eliminates the need for injection. Examples of such alternative routes include transdermal (Rajadgyaksha, V. et al., PCT publication WO 88/04938), nasal (Carey, M. C., et al., U.S. Pat. No. 4,746,508), and pulmonary delivery.

Transdermal administration is not workable for many drugs which cannot penetrate the dermis unless they are formulated with permeation enhancers, such as DMSO, which can cause undesirable side effects. Nasal administration using low-toxicity permeation enhancers of the fusidic acid derivative family has been effective in many instances (Carey, M. C., supra), however, the surface area of nose is relatively small.

Pulmonary delivery offers several potential advantages, particularly in the case of administration of drugs intended to treat conditions affecting the lungs themselves, because some drugs have difficulty reaching the lungs by any route of administration. For instance, Pseudomonas infections in patients with cystic fibrosis can be difficult or impossible to treat, since antibiotics delivered by conventional modes of administration do not easily reach the lungs and therefore cannot stop the spread of infection.

Currently, pulmonary drug delivery methods include mechanical means such as aerosols and inhalers, which have been employed with or without the addition of liposomes to the drug formulation. These methods are effective at getting the drug to the lung, however, they do not ensure efficient transport across the pulmonary surface.

Hayward, J. A. (PCT patent publication #WO 87/01586) discloses using liposomes which contain a drug or diagnostic agent in an aerosol composition for inhalation. Although the liposome-containing drug is more effective than the drug in solution, the drug is still not efficiently administered.

A number of studies have been done which involved the pulmonary administration of lipids for the treatment of respiratory distress. Most of these studies administer liposomes only, without addition of pharmaceutically active substances (Yoshida, T., et al., U.S. Pat. No. 4,571,334). A few groups have investigated the administration of peptides with liposomes for the treatment of respiratory distress (Schilling, et al., U.S. Pat. No. 4,659,805 and Whitsett, J. A., PCT patent publication WO 87/01586). In these cases, however, the lipids were not used as a drug delivery vehicle. Rather the lipid/protein complex was administered to compensate for a deficiency of a normally present lipid/protein complex, which reduces surface tension along the alveolar surfaces.

The compositions and methods of the present invention are widely applicable to a variety of pharmaceutically active substances which for the first time can be efficiently delivered across pulmonary surfaces.

BRIEF DESCRIPTION OF THE INVENTION

The invention provides compositions and methods useful for transporting a pharmaceutically active substance across pulmonary surfaces which avoids some of the problems associated with other modes of delivery. The compositions employed are admixtures comprising: (a) liposomes formed from at least one liposome-forming compound, said liposomes containing an effective amount of a pharmaceutically active substance; and (b) an amount of alveolar surfactant protein effective to enhance transport of the liposomes across a pulmonary surface. The compositions can be administered to the pulmonary surface through a variety of methods such as endotracheal administration. The pharmaceutically active substances contained in the compositions of the invention can be delivered locally for pulmonary action or via the pulmonary surface into the general circulation for systemic action.

The pharmaceutically active substance may be either water soluble or water insoluble. While not wishing to be bound by any particular theory or mechanism of action, it is believed in the case of water soluble substances, the substance is contained in the liposome through encapsulation. Also, it is believed in the case of water insoluble substances, the substance is contained in the liposome through interaction with the hydrophobic portions of the lipids comprising the liposomes.

BRIEF DESCRIPTION OF THE DRAWINGS

FIG. 1 shows the protein sequence of human alveolar surfactant protein SP-A.

FIG. 2 shows the protein sequence of human alveolar surfactant protein SP-B.

FIG. 3 shows the protein sequence of human alveolar surfactant protein SP-C.

DETAILED DESCRIPTION OF THE INVENTION

A. Definitions

Figure 4:
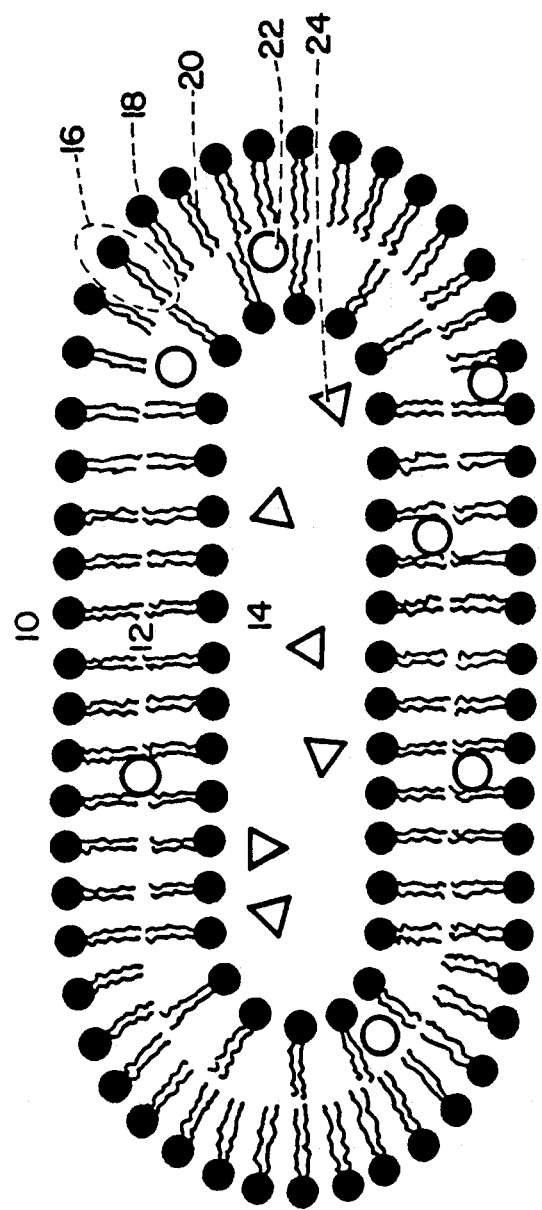
FIG. 4 is a schematic cross-sectional representation of a liposome, which is depicted to contain both water soluble and water insoluble pharmaceutically active substances.

As used herein, "alveolar surfactant protein" refers to the apoproteins associated with alveolar surfactant described herein below. The human lung is composed of a large number of small sacs or alveoli in which gases are exchanged between the blood and the air spaces of the lung. The exchange is mediated by the presence of alveolar surfactant which is a complex substance that lines the epithelial surface of the lung. The surfactant is composed of phospholipid components and protein components. The surfactant-associated protein comprises both serum protein and surfactant-specific apoproteins There are three major surfactant-specific proteins. One is a water-soluble protein having a molecular weight of the order of 32,000 daltons (alveolar surfactant protein SP-A) and the other two are very hydrophobic proteins having molecular weights of the order of about 10,000 daltons (alveolar surfactant protein SP-B and alveolar surfactant protein SP-C) (King, R. J., et al, *Am. J. Physiol.* (1973) 224:788-795). Granular pneumocytes (type II alveolar cells) secrete the surfactant material (Goerke, J., *Biochim. Biophys. Acta* (1974) 344:241-261 and King, R. J., *Fed. Proc.* (1974) 33:2238-2247).

"Alveolar surfactant protein SP-A" refers to the relatively high molecular weight (of the order of 32 kD) apoprotein associated with the lung surfactant complex (Schilling, et al., U.S. Pat. No. 4,659,805). The alveolar surfactant protein SP-A of the invention has an amino acid sequence substantially as shown in FIG. 1.

"Alveolar surfactant protein SP-B" refers to the larger of the two hydrophobic proteins which has a molecular weight of about 18 kD on gels under non-reducing conditions, but which shows a molecular weight of about 10 kD on gels under reducing conditions and has an amino acid sequence substantially as shown in FIG. 2.

"Alveolar surfactant protein SP-C" refers to the smaller of the two hydrophobic proteins which has a molecular weight of about 8 kD or 5 kD on gels and has an amino acid sequence substantially as shown in FIG. 3.

Minor modifications of the above three sequences which do not destroy activity also fall within the definition of alveolar surfactant protein as further set forth below. As is the case for all proteins, the alveolar surfactant proteins can occur in neutral form or in the form of basic or acid addition salts depending on their mode of preparation, or, if in solution, upon its environment. It is well understood that proteins in general, and, therefore alveolar surfactant proteins, in particular, may be found in the form of their acid addition salts involving the free amino groups, or basic salts formed with free carboxyls. Pharmaceutically acceptable salts may, indeed, enhance the functionality of the protein. Suitable pharmaceutically acceptable acid acid addition salts include those formed from inorganic acids such as, for example, hydrochloric or sulfuric acids, or from organic acids such as acetic or glycolic acid. Pharmaceutically acceptable bases include the alkali hydroxides such as potassium or sodium hydroxides, or such organic bases as piperidine, glucosamine, trimethylamine, choline, or caffeine. In addition, the protein may be modified by combination with other biological materials such as lipids and saccharides, or by side chain modification, such as acetylation of amino groups, phosphorylation of hydroxyl side chains, or oxidation of sulfhydryl groups or other modification of the encoded primary sequence. Indeed, in its native form, the alveolar surfactant protein SP-A is a glycosylated protein, and certain of the encoded proline residues have been converted to hydroxyproline. Included within the definition of alveolar surfactant protein SP-A are glycosylated and unglycosylated forms, hydroxylated and nonhydroxylated forms, and any composition of an amino acid sequence substantially similar to that of the native sequences which retains activity. Also included within the definition are fragments of the entire sequence of FIGS. 1, 2, and 3 which retain activity.

It is further understood that minor modifications of primary amino acid sequence may result in proteins which have substantially equivalent or enhanced activity as compared to the native sequences. These modifications may be deliberate, as through site-directed mutagenesis, or may be accidental, such as through mutation of hosts which are alveolar surfactant protein producing organisms. All of these modifications are included as long as activity is retained.

Studies have provided evidence that the phospholipids in the alveolar surfactant are recycled through the lung as part of normal surfactant turnover (Ozarzun, M. J., et al, *Am. Rev. Resp. Disease* (1980) 121:709-721, Hallman, M., et al, *J. Clin. Invest.* (1981) 68:742-751, and Jacobs, H., et al, *J. Dio. Chem.* (1982}257:1085-1810).

The present invention takes advantage of the knowledge that surfactant phospholipid and protein components are taken up by type II cells of the lung. Alveolar surfactant protein SP-A is therefore used to enhance delivery of pharmaceutically active substances which are contained in liposomes.

The mechanism for surfactant phospholipid uptake is currently not understood, but the seeming specificity of the metabolism by type II cells has prompted investigators to consider protein-mediated or protein-directed uptake. In the first studies, the low molecular weight hydrophobic surfactant proteins (alveolar surfactant protein SP-B and alveolar surfactant protein SP-C) were mixed with exogenous phospholipids and formed into liposomes by sonic irradiation (Claypool, W. D., et al, *J. Clin. Invest.* (1984) 74:677-684 and Claypool, W. D., et al, *Exp. Lung Res.* (1984) 6:215-222). The phospholipids used were the major types found in surfactant from mammalian lungs. The hydrophobic proteincontaining liposomes were incubated with isolated type II cells from rat lungs. The amount of lipid transferred was 20-70% above control. This small amount could be attributed to non-specific protein transfer of lipids between cell membranes and liposomes, fusion of the liposome with a cell membrane or merely "sticking" of the liposome to the cells. There also was no cell specificity.

In more recent studies, alveolar surfactant protein SP-A was added to liposomes composed of synthetic phospholipids which were in the appropriate proportions as found in normal alveolar surfactant (Wright, J. R., et al, *J. Biol. Chem.* (1987) 262:2888-2894). The results of incubation of this formulation with type II cells were dramatic. The alveolar surfactant protein SP-A enhanced lipid uptake about 10-20 fold (1000%)

over control. Furthermore, antibodies to alveolar surfactant protein SP-A blocked the lipid uptake by the cells almost completely (95%). In addition the effects seem specific to type II cells and macrophages.

None of the previous studies gave any indication that a pharmaceutically active substance could be included in the liposome-surfactant protein compositions, nor certainly did they show that such a composition would effectively transport the drug across the surface of the lung. The present invention is based on the discovery that delivery of pharmaceutically active ingredients contained in liposomes is rendered more efficient by the addition of alveolar surfactant protein to the delivery vehicle.

The present invention also takes advantage of the knowledge that alveolar surfactant proteins SP-A, SP-B and SP-C have an activity ("ASP activity") which enhances the formation of a lipid film at an air/aqueous interface and causes spreading across the pulmonary surfaces. The spreading activity allows for a greater surface area through which a pharmaceutically active substance can be administered.

"ASP activity" for a protein is defined as the ability, when combined with lipids either alone or in combination with other proteins, to exhibit activity in the in vivo assay of Robertson, B. *Lung* (1980) 158:57-68. In this assay, the sample to be assessed is administered through an endotracheal tube to fetal rabbits or lambs delivered prematurely by Caesarian section. (These "preemies" lack their own alveolar surfactant, and are supported on a ventilator.) Measurements of lung Compliance, blood gases and ventilator pressure provide indices of activity.

Preliminary assessment of activity may also be made by an in vitro assay, for example that of Kihg, R. J., et al, *Am J Physiol* (1972) 223:715-726, or that illustrated below of Hawgood, et al, which utilizes a straightforward measurement of surface tension at an air-water interface when the protein is mixed with a phospholipid vesicle preparation. The alveolar surfactant proteins SP-A, SP-B and SP-C described herein show ASP activity in combination as well as independently. The ASP activity can be used to enhance pulmonary administration of pharmaceutically active substances.

"Pulmonary administration" refers to any mode of administration which delivers a pharmaceutically active substance to any surface of the lung. The modes of delivery can include, but are not limited to those suitable for endotracheal administration, i.e., generally as a liquid suspension, as a dry powder "dust" or as an aerosol. Pulmonary administration can be utilized for both local and systemic delivery of pharmaceutically active substances.

"Transport across a pulmonary surface" refers to any mode of passage which penetrates or permeates the interior surface of the lung. This includes passage through any lung surface, including alveolar surfaces, bronchiolar surfaces and passage between any of these surfaces. Preferably the passage is through alveolar surfaces. Most preferably, the passage is through the type II cells on the alveolar surfaces. Passage can be either directly to the pulmonary tissues for local action or via the pulmonary tissues into the circulatory system for systemic action.

"Liposomes" refers to completely closed vesicular bilayer structures wherein the bilayers have hydrophilic surfaces on either side and a hydrophobic middle as illustrated in FIG. 4. The liposomes are composed of known liposome-forming compounds as described hereinbelow (see, also, Szoka, F. Jr., et al *Ann. Rev. Biophys. Bioeng.* (1980) 9:467-508).

"Liposome-forming compound" refers to any compound capable of forming a liposome either alone or in combination with any other liposome-forming compound(s). Liposomeforming compounds are usually lipids. Liposome-forming compounds generally have polar heads and nonpolar tails as shown in FIG. 4. The polar heads are hydrophilic, while the nonpolar tails are hydrophobic. The polar heads line both the interior and exterior surfaces of the liposome. The nonpolar tails are embedded in the interior of the liposome. Preferred liposome-forming compounds are phospholipids, alone or in combination with simple lipids.

"Phospholipids" refer to amphipathic lipids which are composed of a nonpolar hydrophobic tail, a glycerol or sphingosine moiety, and a polar head. The nonpolar hydrophobic tail is usually a saturated or unsaturated fatty acid group. The polar head is usually a phosphate group attached to a nitrogen-containing base. Exemplary of useful phospholipids are synthetic phospholipids such as phosphatidyl choline, distearoyl phosphatidyl choline, dipalmitoyl phosphatidyl choline, dipalmitoyl phosphatidylethanolamine, etc. and natural phospholipids such as soybean lecithin, egg yolk lecithin, sphingomyelin, phosphatidyl serine, phosphatidyl glycerol, phosphatidyl inositol, diphosphatidyl glycerol, phosphatidylethanolamine, etc. Preferred phospholipids are dipalmitoyl phosphatidyl choline, phosphatidyl choline, and phosphatidyl glycerol.

"Simple lipids" refers to those lipids which do not contain fatty acids. All simple lipids are derived from two major parent classes; the steroids and the terpenes. The preferred simple lipid is cholesterol. Cholesterol is a suitable simple lipid since it is believed to close up the "pores" in the bilayer by occupying spaces between the lipid side chains at the interior, which results in tighter packing and a decrease in permeability. Simple lipids alone do not form liposomes. However, as described above, they are effective liposome-forming substances in combination with phospholipids.

"Pharmaceutically active substance" refers to an agent which is a biologically-active synthetic or natural substance, other than alveolar surfactant proteins themselves, that is useful for treating a medical or veterinary disorder or trauma, preventing a medical or veterinary disorder, or regulating the physiology of a human being or animal. Any pharmaceutically active substance can be delivered using the methods of this invention. Whether the pharmaceutically active substance will reside in the aqueous phase or in the lipid phase of the liposome will determine how the composition is prepared.

Preferred pharmaceutically active substances are those which are useful in treating disorders localized in or near the lungs or respiratory tract, such as infant or adult respiratory distress syndrome, oxygen toxicity associated with respirator therapy, pneumonia, bronchitis, asthma, emphysema, tuberculosis, chronic obstructive pulmonary disorders, and lung cancer. The pharmaceutically active substances which can be used to treat the above disorders include known antivirals, antibacterials, antifungals, antibiotics, antimicrobials, protease inhibitors, anti-oxidants, anti-inflammatory agents, anti-allergenics, xanthines, sympathomimetic amines, mucolytics, corticosteroids, antihistamines, and chemotherapeutic agents.

"Water soluble" pharmaceutically active substance refers to a substance which dissolves in water or is equivalently termed hydrophilic. Such a substance when dissolved in water forms a homogeneous, single phase liquid system. A water soluble pharmaceutically active substance when mixed with liposome-forming compounds will be encapsulated within the liposomes of the invention. Water soluble pharmaceutically active substances are depicted by triangles in FIG. 4. Many substances fall into this definition and include, for example, growth hormone, insulin, tissue plasminogen activator, sodium oxide dismutase, catalase, glucocorticoids, growth factors and antibiotics.

"Water insoluble" pharmaceutically active substance refers to a substance which does not readily dissolve in water or is equivalently termed hydrophobic. All pharmaceutically active substances dissolve in water to a certain degree. However, water insoluble pharmaceutically active substances are not capable of dissolving enough to become a homogeneous, single phase liquid. Water insoluble pharmaceutically active substances associate preferably with the hydrophobic tails of the phospholipids of the present invention. Such substances when mixed with liposome-forming compounds are associated with the hydrophobic middles of the liposomes employed in the invention. Water insoluble pharmaceutically active substances are depicted by circles in FIG. 4. Many substances fall into this definition and include, for example, Vitamin E. Vitamin A, Vitamin D, Vitamin K, and steroids such as progesterone, estrogen, and androgen.

There is a continuum which allows pharmaceutically active substances to be characterized as water soluble or water insoluble, however, the localization of the pharmaceutically active substance in the liposome (association with the hydrophobic tails vs. entrapment amongst the polar heads) is the final determination of classification.

B. Method for Making Compositions of the Invention

The compositions of the present invention are capable of effecting the delivery of pharmaceutically active substances across pulmonary surfaces. The compositions are prepared by mixing liposomes which contain a pharmaceutically active substance with alveolar surfactant protein. Alveolar surfactant proteins SP-A, SP-B and SP-C are each intended for use in the compositions. Alveolar surfactant protein SP-A is the preferred alveolar surfactant protein.

The liposomes of the invention can be made by liposome-forming procedures known in the art (see, e.g., Szoka, F. Jr., et al *Ann. Rev. Biophys. Bioeng.* (1980) 9:467–508). The following methods are illustrative of those that can be used. However, other known liposome-forming procedures may also be employed.

Structurally, there are three principal types of liposomes: multiple compartment liposomes, single compartment liposomes and macrovesicles. Multiple compartment liposomes are multilamellar, while single compartment liposomes and macrovesicles are unilamellar. Multiple compartment liposomes are non-uniform aggregates each containing several layers of phospholipid molecules separated from each other by water molecules. Single compartment liposomes are generally prepared by sonication of multiple compartment liposomes. Macrovesicles are best formed by the slow injection of ether solutions of the lipid into warm aqueous buffer (Deamer, D., et al., *Biochim. Biophys. Acta* (1976) 443:629 ∝ 634). Principally, they are large unilamellar liposomes which can encapsulate approximately ten times more material than single compartment liposomes.

FIG. 4 is a cross-sectional view of a unilamellar liposome. A liposome is a completely closed bilayer composed of one or more liposome-forming compounds 16, one of which is encircled in the FIGURE. The liposome-forming compounds are each made up of a polar head 18 and a non-polar, hydrophobic tail 20. The hydrophobic nature of the non-polar tails of the liposome-forming substances causes the non-polar tails to associate with other non-polar tails, to form a hydrophobic environment. There is thus formed a hydrophobic phase 12 which is disposed within the bilayered structure. The polar heads of the liposome-forming substances tend to associate with the hydrophilic environment. Water insoluble pharmaceutically active substances, 22 when added to a liposome preparation, become associated with the hydrophobic phase 12. The hydrophilic nature of the polar heads of the liposome-forming substances causes them to be orientated away from the hydrophobic interior, thereby forming an exterior hydrophilic surface 10 and an interior hydrophilic surface 14. Water soluble pharmaceutically active substances 24, when added to a liposome preparation, become encapsulated in the hydrophilic interior of the liposome, within the interior hydrophilic surface 14.

Multiple compartment or multilamellar liposomes are most commonly prepared by admixing in a vessel liposomeforming compounds, such as, phospholipid, cholesterol and other hydrophobic molecules in the presence of an organic solution, preferably chloroform. The organic solution is then evaporated, preferably by rotary evaporation, leaving a thin film of lipid on the wall of the vessel. Subsequently, the thin film of lipid is removed from the wall of the vessel by shaking with aqueous buffer solutions. This process yields multicompartment or multilamellar liposomes.

Sonication of multicompartment liposomes results in the formation of fairly uniform single compartment vesicles. Gel filtration and/or ultracentrifugation separate the single compartment liposomes from the multilamellar ones (Fendler, J. H., et al., *Life Sciences* (1977) 20:1109–1120).

Both water soluble and water insoluble pharmaceutically active substances can be incorporated in liposomes. To prepare liposomes containing water insoluble pharmaceutically active substances, the latter are dissolved in an organic solvent, such as chloroform, along with liposome-forming substances. The chloroform is then evaporated, for example in a rotary evaporator, whereupon the water insoluble pharmaceutically active substances become embedded in the thin film of liposomes deposited on the wall of the vessel. The liposomes are reconstituted by the addition of aqueous buffer. The water insoluble pharmaceutically active substance is associated with the hydrophobic phase of the liposome upon aqueous reconstitution.

To prepare liposomes containing water soluble pharmaceutically active substances, liposomes are first prepared, for example, by the previously described method involving rotary evaporation of the liposome-forming substances. The resultant thin film of evaporated liposome-forming substances which is deposited on the wall of the vessel is reconstituted by the addition of an aqueous buffer which contains the water soluble pharmaceutically active substance, thereby forming liposomes which contain entrapped water soluble pharmaceutically active substances. The water soluble pharmaceutically active substances have become incorporated in the aqueous phase of the liposomes. The liposomes containing the entrapped water soluble pharmaceutically active substance can be readily separated from the excess free water soluble pharmaceutically active substance by gel filtration using, for example, a Sephadex G-50 column. Once the water soluble pharmaceutically active substance is entrapped in the liposome, it can only be liberated by leakage through the bilayer of the liposome or by destruction of the vesicle.

In order to prepare the composition of the invention, the alveolar surfactant protein SP-A is admixed with the reconstituted liposome suspension containing the pharmaceutically active substance. This may be accomplished by adding the alveolar surfactant protein either during or after reconstitution of the liposomes. When alveolar surfactant proteins SP-B or SP-C are included in the composition of the invention, the alveolar surfactant protein SP-B or SP-C is admixed in an organic solvent with the liposome-forming substances and the preparation of the composition proceeds as described above.

C. Formulation and Administration

The composition of the present invention is prepared by forming liposomes which comprise at least one iposome-forming compound, an effective amount of a pharmaceutically active substance, and alveolar surfactant protein in an amount effective to transport the composition across a pulmonary surface. Alveolar surfactant protein can include alveolar surfactant proteins SP-A, SP-B, and SP-C. Alveolar surfactant protein SP-A is preferred. The formulation of the composition comprises about 20% to 99.9% by weight liposome-forming compounds, 40% to less than 1% by weight pharmaceutically active substance, and 40% to less than 1% alveolar surfactant protein, based on the weight of the composition exclusive of water. Preferably, the composition of the invention comprises 60-90% by weight liposome-forming compounds, 5-20% by weight pharmaceutically active substance and 5-20% by weight alveolar surfactant protein, exclusive of water.

The liposome-forming portion of the composition preferably contains one or more compounds selected from dipalmitoyl phosphatidyl choline, phosphatidyl choline, phosphatidyl glycerol, triacylglycerols, palmitic acid and cholesterol. The liposome-forming portion of the composition preferably comprises 1-90% dipalmitoyl phosphatidyl choline, 1-90% phosphatidyl choline, 1-30% phosphatidyl glycerol and 1-30% cholesterol based on the weight of the liposome-forming portion of the composition.

The compositions of the present invention are preferably administered in a form suitable for endotracheal administration, i.e., generally as a liquid suspension, as a dry powder "dust" or as an aerosol. For direct endotracheal administration, the composition is suspended in a liquid with suitable excipients such as, for example, water, saline, dextrose, or glycerol and the like. The compositions may also contain small amounts of non-toxic auxiliary substances such as pH buffering agents, for example, sodium acetate or phosphate. To prepare the "dust", the composition prepared as described above, is lyophilized, and recovered as a dry powder.

If to be used in aerosol administration, the composition is supplied in finely divided form along with a propellant. Useful propellants are typically gases at ambient conditions, and are condensed under pressure. Lower alkanes and fluorinated alkanes, such as Freon$^R$, may be used. The aerosol is packaged in a container equipped with a suitable valve so that the ingredients may be maintained under pressure until released.

Administration of liquid suspension, dry powder "dust", or aerosol is through inhalation of the composition into the lung via the trachea.

The compositions of the present invention may also be administered during bronchoscopy procedures.

The compositions of the present invention are administered in an amount suitable for the condition and the subject being treated and the subject. The amount of pharmaceutically active substance can vary widely depending on the particular pharmaceutically active substance and its use. Generally, the effective amount for any given pharmaceutically active substance is known. Hormones are usually administered in the nanogram range, while it is not uncommon for chemotherapeutics to be administered in the range of 10 milligrams. Amounts of pharmaceutically active substance between about 1 ng and 10 mg are administered in one dose. The number of doses necessary is dependent on the condition being treated.

D. Uses

The compositions of the present invention can be used to administer a wide range of pharmaceutically active substances efficiently across pulmonary surfaces. The compositions of the invention can be useful for systemic delivery of pharmaceutically active substances as well as local delivery of pharmaceutically active substances.

A variety of lung-specific diseases such as infant respiratory distress syndrome, adult respiratory distress syndrome, viral pneumonia, bacterial pneumonia, Group B streptococcal infection, oxygen toxicity, alpha-1-anti-protease deficiency, emphysema, asthma, tuberculosis, lung cancer, bronchitis, etc. could be treated successfully with an administration system which could deliver pharmaceutically active substances directly across the pulmonary surfaces. The pharmaceutically active substances that can be administered for these diseases include, but are not limited to, antivirals such as acyclovir, zidovudine, and ribavarin; antibacterials such as sulfamethoxazole and nalidixic acid; fungicides such as fungizone and mycostatin; antibiotics such as cephalosporins, penicillins, tetracyclines and aminoglycosides: protease inhibitors such as alpha-1-anti-protease; anti-oxidants such as vitamin E, vitamin C, superoxide dismutase and catalase: anti-inflammatory agents such as prostaglanins, salicylates, pyrazolons, propionic acid derivatives and para-aminophenol derivatives; anti-allergics such as antihistamines, including terfenadine, diphenhydramine, chlorpheniramine and promethazine: methyl xanthines such as theopbylline and $\beta$-adrenergic agonists: sympathomimetic amines such as epinephrine, phenylephrine, pseudoephedrine, isoproterenol and albuterol; mucolytics such as acetyl cysteine; corticosteroids such as dexamethasone and triamcinolone and; chemotherapeutic agents such as alkylating agents (nitrogen mustards, alkyl sulfonates, nitrosoureas and triazenes) and antimetabolites (folic acid derivatives, pyrimidine derivatives, and purine derivatives).

Many of the indications that may find utility in the present invention are a direct result and/or effect of infant respiratory distress syndrome or adult respiratory distress syndrome. In these circumstances the transport of pharmaceutically active substances across a pulmonary surface could be used as an adjunct to conventional lung surfactant replacement therapy. Viral pneumonia can be treated with antiviral agents. Bacterial pneumonia can be treated with antibacterial agents and antibiotics. Group B streptococcal infection can be treated with antibiotics. Oxygen toxicity can be treated with vitamin E, vitamin C, superoxide dismutase and catalase. Superoxide dismutase and catalase are the enzymes involved with the metabolism of superoxide anion and hydrogen peroxide, respectively.

Pneumonia not associated with infant respiratory distress syndrome may also benefit from delivery of anti-virals and/or antibiotics.

Therapy for emphysematous disease as well as congenital alpha-1-antiprotease deficiency could be treated with anti-proteases.

Another lung-specific use would be bacterial infections which are difficult to treat with systemic administration of antibiotics or with antibiotics that have substantial side effects. An example of this would be pentamidine isethionate treatment of *Pneumocystis carinii*. Pentamidine isethionate is quite toxic if given systemically. Also lung-specific administration yields higher local doses.

Chemotherapeutic agents can be administered in a lung-specific fashion which would yield higher local doses. The administration may be given during bronchoscopy.

Methyl xanthines, including theophylline and $\beta$-adrenergic agonists, can be delivered for asthma.

Since this administration system can also transport pharmaceutically active substances directly into the general circulation, a variety of pharmaceutically active substances which would act in a systemic fashion can also utilize this system. These pharmaceutically active substances include insulin, growth hormone, other peptide hormones, thrombolytics, fibroblast growth factor, calcitonin, vasopresin, renin, prolactin, thyroid stimulating hormone, corticotropin, follicle stimulating hormone, luteinizing hormone, chorionic gonadotropin, atrial peptides, interferon, tissue plasminogen activator, gammaglobulin, and Factor VIII, to name but a few.

EXAMPLES

Many of the techniques which are used to make liposomes and assay performance are widely practiced in the art, and most practitioners are familiar with the standard resource materials which describe specific conditions and procedures. The examples are written in observation o; such knowledge and incorporate by reference procedures considered conventional in the art. The following examples are intended to illustrate the invention, without acting as a limitation upon its scope.

A. Liposome Preparation

The liposomes of examples 1-5 were prepared using the following general procedure. All lipids were obtained from Avanti Polar Lipids (Birmingham, AL). Unilamellar liposomes were prepared in minimal essential medium containing Kreb's improved salts (Dawson, R. M. C., et al., *Data for Biochemical Research* (1969), p. 507 Clarendon Press, Oxford), 2 mM sodium pyruvate, 13 mM glucose, and 25 mM HEPES, pH 7.4 (MEM-Krebs) as described by the French pressure cell method of Hamilton, et al., *J. Lipid Res.* (1980) 21:981-992. Briefly, liposomes were made by admixing in a chloroform solution dipalmitoyl phosphatidyl choline, phosphatidyl choline, phosphatidyl glycerol and cholesterol in the weight ratios of 5:10:2:1.5, respectively. The chloroform is evaporated from the mixture by rotary evaporation. The dried lipids were rehydrated in MEM-Krebs and sheared to form unilamellar liposome vesicles by French pressure cell. Alternatively sonication can be employed to form the unilamellar vesicles.

B. In Vitro Assay

Type II Cell Isolation and Incubation

The in vitro assay employed in examples 1 and 4 was performed by the following general procedure. Freshly isolated type II cells were prepared by the method of Dobbs, et al., *Am. Rev. Respir. Sid.* (1986) 134:141-145. Briefly, lungs of specific-pathogen-free male Sprague-Dawley rats weighing 160-180 g (Bantin-Kingman, Fremont, CA) were digested with elastase (Cooper Biomedical, Malverne, PA). The minced digest was filtered through a series of nylon meshes and cells were collected by centrifugation. The cells were then plated on IgG-coated plates and the non-type II cells, which were primarily macrophages and lymophocytes, adhered to the plate over a period of one hour at 37° C. in a 10% $CO_2$/air incubator. The non-adherent cells were removed by gentle panning and were centrifuged at 130×g for 8 minutes. This cell pellet contained 85±1% type II cells. The viability of the cells as determined by erythrosin B exclusion averaged 97±1%.

$2.5 \times 10^6$ freshly isolated type II cells were suspended in 1 ml of MEM-Krebs. The concentration of calcium was 2 $\mu$M. The cells were incubated at 37 or 4° C. in 15 ml centrifuge tubes tilted at an angle of approximately 25° from horizontal in order to enhance mixing. Liposomes which contain radiolabelled protein were added. After mixing, the cells were incubated at 37° or 4° C. for various lengths of time. At the end of the incubation period, 4 ml of MEM-Krebs at 4° C. was added to cells, and the cells and media were separated immediately by centrifugation at 140×g for 10 minutes in a Damon International CRU-5000 Centrifuge using a number 269 rotor (International Equipment Co., Needham Heights, MA). The medium was removed and the cells were gently resuspended. The cells were transferred to a fresh tube and washed twice more by centrifugation. Zero time values were determined by centrifugation and washing of the cells immediately after addition of liposomes. The actual elapsed time before the beginning of the first centrifugation was 2-3 minutes. The final cell pellet was resuspended in 0.5 ml of MEM-Krebs; 0.3 ml was analyzed for radioactivity in a Beckman LS-75000 scintillation counter. A cell count was obtained using a Neubauer counting chamber.

C. In Vivo Assay

Anesthetized Rat Model

The in vivo assay employed in examples 2 and 3 was performed by the following general procedure. The compositions were administered to the lungs of anesthetized adult Sprague-Dawley rats by endotracheal cannula. At various times after administration of the compositions, the animals were sacrificed by overdosing with anesthetics. The lungs and serum were obtained from each rat for analysis. The lung tissue was minced and extracted with 2:1 chloroform:methanol. The serum was extracted with 2:1 chloroform:methanol. The serum was sampled to get an indication of the amount of pharmaceutically active substance being transported into general circulation.

EXAMPLE 1

LIPOSOMES CONTAINING VITAMIN E IN VITRO

Vitamin E is a water-insoluble pharmaceutically active substance with antioxidant properties. Premature infants require supplements of Vitamin E. Furthermore, administration of vitamin E may be a beneficial adjunct to conventional lung surfactant therapy for premature infants because it may protect against oxidant lung injury.

Liposomes were prepared as described in section A with the addition of $^3$H-Vitamin E in the lipid mixture before evaporation. The following weight ratios of lipid and Vitamin E were used to prepare the liposomes:
DPPC:PC:PG:Cholesterol:Vitamin E

```
DPPC:PC:PG:Cholesterol:Vitamin E
  5    10  2    1.5         1.5
```

The chloroform was evaporated from the lipid/Vitamin E mixture by rotary evaporation. The dried lipid/Vitamin E mixture was rehydrated in MEM-Krebs to a concentration of 87 μg Vitamin E/ml. Alveolar surfactant protein SP-A was added to the liposome mixture to a concentration of 100 μg/ml. 100 μl of the liposome mixture in the presence and absence of alveolar surfactant protein SP-A was added to 1 ml of freshly isolated type II cells and assayed as described above in section A. The washed cell pellets were analyzed for radiolabelled Vitamin E incorporation at 0 and 60 minutes by counting in a Beckman LS-7500 scintillation counter with the following results:

|  | TIME | |
|---|---|---|
|  | 0 min* | 60 min* |
| Liposomes + alveolar surfactant SP-A | 17.9 | 85.9 |
| Control Liposomes (no alveolar surfactant SP-A) | 6.8 | 28.4 |

*data expressed as ng Vitamin E/10$^6$ cells

This data indicates that the alveolar surfactant protein SP-A stimulates the uptake of liposomes containing Vitamin E.

EXAMPLE 2

LIPOSOMES CONTAINING VITAMIN E IN VIVO 60 MINUTE TIMECOURSE

The liposomes containing Vitamin E prepared as in Example I above were tested in vivo by administration to rats according to the procedure outlined above in section C. The animals were sacrificed at 0 and 60 minutes and the lungs were tested for incorporation of radiolabelled Vitamin E as described above, with the following results:

|  | TIME | |
|---|---|---|
|  | 0 min* | 60 min* |
| Liposomes + alveolar surfactant SP-A | 505 | 10,409 |
| n = 2 | 534 | 3,719 |
| Control Liposomes | 299 | 914 |
| (no alveolar surfactant SP-A) | 235 | 926 |
| n = 2 |  |  |

*data expressed as dpm

The data indicates that alveolar surfactant protein SP-A stimulates the transport of the liposomes containing Vitamin E to lung tissue in a rapid fashion.

EXAMPLE 3

LIPOSOMES CONTAINING VITAMIN E IN VIVO 24 HOUR TIMECOURSE

The liposomes containing Vitamin E prepared as in Example I above were tested in vivo by administration to rats according to the procedure outlined above in section C. The animals were sacrificed at 1 and 24 hours. The lungs and serum were tested for incorporation of radiolabelled Vitamin E with the following results:

|  | TIME | |
|---|---|---|
|  | 1 hour* | 24 hours* |
| LUNG |  |  |
| Liposomes + alveolar surfactant SP-A | $2.8 \times 10^6$ | $1.4 \times 10^6$ |
| Control Liposomes (no alveoloar surfactant SP-A) | $2.4 \times 10^5$ | $1.2 \times 10^6$ |
| Serum |  |  |
| Liposomes + alveolar surfactant SP-A | $2.1 \times 10^4$ | $5.8 \times 10^3$ |
| Control Liposomes (no alveolar surfactant SP-A) | $8.6 \times 10^3$ | $4.5 \times 10^3$ |

*data expressed as cpm

The data indicates not only that the alveolar surfactant protein SP-A enhances transport to the lung, but it also enhances serum levels of radiolabelled vitamin E. The transport of Vitamin E into the serum probably reflects transport through pulmonary surfaces into the general circulation. At 24 hours, the amount of radiolabelled Vitamin E in the lung is comparable in experimental and control animals, reflecting continued non-specific uptake after the initial increase due to the addition of alveolar surfactant protein SP-A. The same non-specific effect is also seen in the serum.

EXAMPLE 4

LIPOSOMES CONTAINING WATER SOLUBLE SUBSTANCE IN VITRO

The water soluble substance 6-carboxy-fluorscein was encapsulated in liposomes and tested for transport into type II cells in vitro. The liposomes were prepared as described above in section A. The dried lipids were rehydrated in MEM-Krebs to which 1% (w/v) 6-carboxy-fluorscein had been added. The 6-carboxy-fluorscein not contained within the liposome was removed by gel filtration chromatography. Alveolar surfactant protein SP-A was added to the liposome mixture to a concentration of 100 μg/ml. 100 μl of the liposome mixture in the presence and absence of alveolar surfactant protein SP-A is administered to 1 ml of freshly isolated type II cells and assayed as described above in section B. The cells were analyzed for ability to fluoresce after 60 minutes as follows:

| Liposomes + alveolar surfactant SP-A* | 2.5 |
|---|---|
| n = 2 | 3.3 |
| Control Liposomes* | 0.9 |
| (no alveolar surfactant SP-A) | 0.4 |
| n = 2 |  |

*data expressed as AFU (arbitrary fluorescence units)

6-carboxy-fluorscein was used as a model system for the assessment of delivery of water soluble pharmaceutically active substances. In this model system alveolar surfactant protein SP-A also stimulates the uptake of liposomes containing the water soluble substance 6-carboxy-fluorscein.

Modifications of the above described modes for carrying out the invention that are obvious to those of skill in the art are intended to be within the scope of the following claims.

We claim:

1. A composition for pulmonary administration of a pharmaceutically active substance, said composition comprising 60–90% by weight liposome forming compound, 5–20% by weight pharmacentically active substance, and 5–20% by weight surfactant protein, based on the total weight of liposome-forming substance, pharmacentically active substance and alveolar surfactant protein, wherein said composition comprises liposomes.

2. The composition of claim 1 wherein said alveolar surfactant protein comprises at least one alveolar surfactant protein selected from alveolar surfactant protein SP-A, alveolar surfactant protein SP-B, and alveolar surfactant protein SP-C.

3. The composition of claim 1 wherein said pharmaceutically active substance is water insoluble.

4. The composition of claim 1 wherein said pharmaceutically active substance is water soluble.

5. The composition of claim 3 wherein said pharmaceutically active substance is Vitamin E.

6. The composition of claim 1 wherein said liposome-forming compound comprises 1–90% by weight dipalmitoyl phosphatidyl choline, 1–90% by weight phosphatidyl choline, 1–30% by weight phosphatidyl glycerol, and 1–30% by weight cholesterol.

7. A method of administering a pharmaceutically active substance which comprises applying to pulmonary surfaces for transport across said surfaces a composition comprising:
   (a) liposomes formed from at least one liposome-forming compound, said liposomes containing an effective amount of a pharmaceutically active substance; and
   (b) alveolar surfactant protein in an amount effective to enhance transport of said liposomes across a pulmonary surface.

8. The method of claim 7 wherein said composition is applied to the pulmonary surfaces in the form of an aerosol spray.

9. A method of preparing a composition for delivering a pharmaceutically active substance comprising:
   (a) forming liposomes containing at least one liposome-forming compound and an effective amount of a pharmaceutically active substance; and
   (b) adding alveolar surfactant protein in an amount effective to enhance transport of said liposomes across a pulmonary surface.

* * * * *